(12) United States Patent
Jarvis

(10) Patent No.: US 8,083,973 B2
(45) Date of Patent: Dec. 27, 2011

(54) POLYCHROMIC SUBSTANCES AND THEIR USE

(75) Inventor: Anthony N Jarvis, Cheshire (GB)

(73) Assignee: DataLase Ltd., Cheshire (GB)

( * ) Notice: Subject to any disclaimer, the term of this patent is extended or adjusted under 35 U.S.C. 154(b) by 0 days.

(21) Appl. No.: 12/863,625

(22) PCT Filed: Jan. 22, 2009

(86) PCT No.: PCT/GB2009/000174
§ 371 (c)(1),
(2), (4) Date: Oct. 6, 2010

(87) PCT Pub. No.: WO2009/093028
PCT Pub. Date: Jul. 30, 2009

(65) Prior Publication Data
US 2011/0017961 A1     Jan. 27, 2011

(30) Foreign Application Priority Data

Jan. 25, 2008  (GB) .................................. 0801440.9

(51) Int. Cl.
*G02B 5/23*     (2006.01)
*C07C 223/00*   (2006.01)
*C07C 235/00*   (2006.01)
*C07C 237/00*   (2006.01)
*C07C 239/00*   (2006.01)

(52) U.S. Cl. ........ 252/586; 564/159; 564/204; 564/259; 430/270.1; 430/270.15

(58) Field of Classification Search ................... 252/586; 564/204, 159; 528/310, 318, 322, 332, 335, 528/336, 354, 363, 392, 422; 430/270.1, 430/270.15, 330, 9, 905, 913, 944, 945
See application file for complete search history.

(56) References Cited

U.S. PATENT DOCUMENTS 5,095,134 A * 3/1992 Liu ................................ 560/24
6,541,601 B1 * 4/2003 Hollingsworth et al. ..... 528/310
2003/0103905 A1   6/2003 Ribi
2007/0019790 A1 * 1/2007 Lewis et al. ................... 378/163

FOREIGN PATENT DOCUMENTS

| | | |
|---|---|---|
| JP | 02-202923 | 8/1990 |
| WO | WO 2004/060852 | 7/2004 |
| WO | WO 2005/036109 | 4/2005 |
| WO | WO 2006/018640 | 2/2006 |
| WO | WO 2007/063332 | 6/2007 |
| WO | WO 2007/071971 | 6/2007 |
| WO | WO 2007/071971 A1 * | 6/2007 |

OTHER PUBLICATIONS

Bliznyuk, V. et al., "Interaction between adjacent two-dimensional lattices of diacetylenic lipid and a cyanine dye," *Thin Solid Films*, 1994, pp. 1037-1042, vol. 244.
Datbase Caplus [Online], Bergel'son, L. et al., "Tri-and tetraacetylenic macrocyclic lactones," *Izvestiya Akademii Nauk SSSR, Seriya Khimicheskaya*, 1962, pp. 539-540, DN: 57:55710, Accession No. 1962:455710.
Datbase Caplus [Online], Heaney, H. et al., "Product class 4: organometallic complexes of copper," *Science of Synthesis*, 2004, pp. 305-662, vol. 3, DN: 141:242819, Accession No. 2003:1000504.
Ohba, S. et al., "Synthesis of Novel Amphiphilic Diacetylenes with Amino or Ammonium Functionality," *Tetrahedron*, 1991, pp. 9947-9952, vol. 47, No. 47.
Vlasov, V.M. et al., "Vinyl ethers and acetals of diacetylenic glycols," *Zhurnal Organicheskoi Khimii*, 1971, pp. 1348-1349, vol. 7, No. 7.

* cited by examiner

*Primary Examiner* — Ling Choi
*Assistant Examiner* — Bijan Ahvazi
(74) *Attorney, Agent, or Firm* — Saliwanchik, Lloyd & Eisenschenk

(57) ABSTRACT

A compound which undergoes a color change upon irradiation, and which has the general structure: $X-C\equiv C-C\equiv C-Y-(CO)_n-QZ$ wherein X is H, alkyl or $-Y-(CO)_n-QW$; each Y is the same or a different divalent alkylene group; Q is O, S or NR; R is H or alkyl; W is H, alkyl or Z; each Z is the same or a different unsaturated alkyl group; and each n is 0 or 1.

18 Claims, No Drawings

POLYCHROMIC SUBSTANCES AND THEIR USE

CROSS REFERENCE TO A RELATED APPLICATION

This application is a National Stage Application of international Application Number PCT/GB2009/000174, filed Jan. 22, 2009; which claims priority to Great Britain Application No. 0801440.9, filed Jan. 25, 2008; which are incorporated herein by reference in their entirety.

FIELD OF THE INVENTION

This invention relates to polychromic substances and their use.

BACKGROUND OF THE INVENTION

Diacetylenes can be coloured, or made to change colour, and have properties that make them suitable for use in sensors. Their use in multi-colour printing is disclosed in, for example, WO2006/018640. A particularly preferred diacetylene for this purpose is 10,12-pentacosadiynoic acid (PDA).

WO03/046050 discloses amide polymers with 10,12-PDA type side chains.

SUMMARY OF THE INVENTION

According to the present invention, a novel compound is of the type that will undergo a colour change upon irradiation, and which has the general structure:

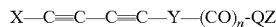

wherein X is H, alkyl or —Y—(CO)$_n$-QW; each Y is the same or a different divalent alkylene group; Q is O, S or NR; R is H or alkyl; W is H, alkyl or Z; each Z is the same or a different unsaturated alkyl group; and each n is 0 or 1.

According to a second aspect of this invention, a method of imparting colour to a material including a compound as defined above, comprises subjecting the material to irradiation. The compound may be in or on the material.

DESCRIPTION OF PREFERRED EMBODIMENTS

It will be appreciated that compounds of the invention are ethers, thioethers, amides or derivatives of carboxylic acids. Each alkyl or alkylene group typically includes up to 20 or more carbon atoms, and may be cyclic or acyclic, saturated or unsaturated, aliphatic or aromatic.

It may be preferred that the group R includes unsaturation. Z includes unsaturation, e.g. a further diacetylene structure, such that the compound is a dimer. The unsaturation in Z is not conjugated to the diacetylene part of the molecule. X or Z may be substituted, e.g. X is substituted with (CO)$_n$-QZ, so that the compound is difunctional.

The presence of the group Z has the effect of increasing compatibility with thermoplastics. This can enhance processability and resistance to phase separation/migration. We believe that because Z includes an unsaturated, e.g. C=C or C≡C, bond, this can undergo cross-linking and/or polymerisation, thus locking the chain in the state that is coloured.

The carboxylic acids from which the compounds of the invention are derived include compounds that are known or can readily be prepared by one of ordinary still in the art. A particularly preferred example of such an acid is PDA, and its carboxylic acid derivatives include esters, thioesters and amides.

The diacetylene compound may comprise other functional groups known in organic chemistry such as alcohol, amino, carbonyl such as aldehyde or ketone, carboxylic acid or carboxylic acid derivatives, ether, halogeno, alkene, alkyne, nitro, nitrile or any type of aliphatic or aromatic ring and the like. Preferred examples are alcohol group derivatives such as ethers. Particularly preferred examples are carboxylic acid derivative groups such as esters, thioesters, anhydrides and amides.

Starting diacetylene compounds which include carboxylic acid groups are preferred as they can be easily converted into carbonyl chloride groups by reaction with a chlorinating agent such as oxalyl chloride or thionyl chloride and the like. The carbonyl chloride intermediate compound can then react with nucleophilic species such as alcohols, thiols, amines or carboxylate groups to yield the desired ester, thioester, amide or anhydride diacetylene compounds. The resultant ester, thioester, amide or anhydride group diacetylene compounds can be mono-functionalized by reacting the carbonyl chloride group with a co-reactant molecule comprising just one nucleophilic group, or the co-reactant molecule can comprise at least two nucleophilic groups to produce a desired compound that comprises more than one diacetylene moiety. Particularly preferred are amines which react to give rise to amides. Any primary amine, secondary amine or tertiary amines is suitable. The amine can comprise one nucleophilic nitrogen such as 1-aminobutane or propargylamine, or at least two nucleophilic nitrogen groups such as ethylenediamine or 1,12-diaminododecane.

More particularly preferred are the carboxylic acid derivatives of 10,12-pentacosadiynoic acid such as esters, thioesters, anhydrides and amides. More particularly preferred still are amide derivatives comprising the —CONR— group, where R is H or any group comprising at least one carbon atom. These can be produced by reacting 10,12-pentacosadiynoic acid with a chlorinating agent which converts the carboxylic acid group into a carbonyl chloride followed by reaction with an amine.

Diacetylene compounds that can be used to form compounds for use in the present invention include diacetylene mono and dicarboxylic acids, such as the diacetylene monocarboxylic acid 10,12-pentacosadiynoic acid and the diacetylene dicarboxylic acid 10,12-docosadiyndioic acid; diacetylene mono and dialcohols; diacetylene mono and diamines, diacetylene mono and dithiols and combinations thereof such as diacetylene hydroxy-carboxylic acid compounds.

Diacetylene compounds that can be used, to form compounds for use in the present invention include, but are not limited to, 5,7-docosadiyndioic acid, 5,7-dodecadiynoic acid, 4,6-dodecadiynoic acid, 5,7-eicosadiynoic acid, 5,7-eicosadiyn-1-ol, 6,8-heneicosadiynoic acid, 8,10-heneicosadiynoic acid, 12,14-heptacosadiynoic acid, 2,4-heptadecadiynoic acid, 4,6-heptadecadiynoic acid, 2,4-heptadecadiyn-1-ol, 5,7-hexadecadiynoic acid, 2,10,12-heneicosaadiynoic acid, 10,12-heptacosadiynoic acid, 10,12-docosadiyndioic acid, 10,12-octadecadiynoic acid, 10,12-pentacosadiynoic acid, 10,12-tricosadiynoic acid, 2,4-hexadiyne-1,6-diol, 1,6-bis-(4-methoxy-phenyl)-1,6-diphenyl-hexa-2,4-diyne-1,6-diol, 1,1,1,8,8,8-hexaphenyl-octa-3,5-diyne-2,7-diol, 1,1,6,6-tetrakis-(3-methoxy-phenyl)-hexa-2,4-diyne-1,6-diol, 1,1,6,6-tetrakis-biphenyl-4-yl-hexa-2,4-diyne-1,6-diol, 1,1,6,6-tetraphenyl-hexa-2,4-diyne-1,6-diol, 10,12-pentacosadiynol and derivatives thereof.

Other diacetylene carboxylic acid and alcohol compounds that can be used to form compounds for use in the present invention include, but are not limited to, 4,6-decadiyn-1,10-diol, 2,7-dimethyl-3,5-octadiyn-2,7-diol, 5,7-dodecadiyndioic acid, 5,7-dodecadiyn-1,12-diol, 5,7-eicosadiyn-1-ol, 10,12-heneicosadiynoic acid, 4,6-heptadecadiynoic acid, 2,4-heptadecadiyn-1-ol, 2,4-hexadiyn-1,6-diol, 14-hydroxy-10,12-tetradecadiynoic acid, 6,8-nonadecadiynoic acid, 5,7-octadecadiynoic acid, 3,5-octadiyn-1,8-diol, 5,7-tetradecadiynoic acid, 10,12-tricosadiynoic acid. Further examples of diacetylene compounds include 1,6-bis-(4-methoxy-phenyl)-1,6-diphenyl-hexa-2,4-diyne-1,6-diol, 1,1,1,8,8,8-hexaphenyl-octa-3,5-diyne-2,7-diol, 1,1,6,6-tetrakis-(3-methoxyphenyl)-hexa-2,4-diyne-1,6-diol, 1,1,6,6-tetrakis-biphenyl-4-yl-hexa-2,4-diyne-1,6-diol, 1,1,6,6-tetraphenyl-hexa-2,4-diyne-1,6-diol and derivatives thereof.

Particularly preferred diacetylene compounds used to form the compounds of the present invention are those that possess one or two carboxylic acid groups. Examples of such compounds include the diacetylene monocarboxylic acid compound 10,12-pentacosadiynoic acid and the diacetylene dicarboxylic acid compound 10,12-docosadiyndioic acid. The diacetylene compounds of the present invention include carboxylic acid derivatives such as esters, amides and thioesters that are formed using alcohol, amine or thiol compounds that include unsaturation. The term 'unsaturation' includes double and triple bonds groups such as $C{=}C$ and $C{\equiv}C$. Particularly preferred unsaturated groups are terminal monoacetylene groups —$C{\equiv}C$—H. Particularly preferred examples can be provided by reacting a diacetylene mono or dicarboxylic acid compound with a propargyl, alkylpropargyl or dialkylpropargyl compound such as propargyl alcohol, propargylamine and N-alkyl derivatives thereof, propargyl thiol, and 1-methyl and 1,1-dimethyl derivatives thereof such as, 2-amino-but-3-yn, 3-butyn-2-ol, 1,1-dimethylpropargylamine and 2-methyl-3-butyn-2-ol and dipropargylamine and tripropargylamine and derivatives thereof.

Particularly preferred examples can be provided by reacting a diacetylene mono or dicarboxylic acid compound with a propargyl, alkylpropargyl or dialkylpropargyl compound such as propargyl alcohol, propargylamine and N-alkyl derivatives thereof, propargyl thiol, and 1-methyl and 1,1-dimethyl derivatives thereof such as 2-amino-but-3-yn, 3-butyn-2-ol, 1,1-dimethylpropargylamine and 2-methyl-3-butyn-2-ol, dipropargylamine, tripropargylamine and derivatives thereof.

Preferred compounds possess at least one alcohol derivative group such as ether. More preferred compounds possess at least one carboxylic acid derivative group such as ester, thioester, amide or anhydride. A specifically preferred acid is 10,12-pentacosadiynoic acid, and its carboxylic acid derivatives such as esters, thioesters, anhydrides and amides of 10,12-pentacosadiynoic acid are particularly preferred. The diacetylene compound can be non-ionic, zwitterionic, cationic or anionic.

Particularly preferred compounds are those that are initially colourless or of low visual colour, and become coloured upon irradiation. More preferred are those that are initially colourless or of low visual colour, and become coloured upon irradiation and will then change to a colour, different to the first, upon further irradiation with the same or different type of radiation.

Any type of radiation which performs the colour change reactions can be used. This includes laser or non-coherent, broadband or monochromatic radiation. Specific radiation types include ultraviolet, near, mid or far infrared, visible, microwave, gamma-ray, x-ray or electron beam.

Particularly preferred are those examples that change from colourless or low visual colour to coloured on exposure to ultraviolet irradiation, and then change to a colour different to the first on subsequent exposure to infrared irradiation.

Laser irradiation is preferred for writing text and drawing artwork directly on substrates comprising the compounds of the present invention, as laser imaging can be conveniently controlled by computer with the appropriate software. However similar effects can also be obtained by passing radiation through a mask before it reaches the substrate comprising the compounds of the present invention.

The diacetylene compounds of the present invention can be used singularly or in admixture with other types of compound that will undergo colour change reactions on irradiation. Preferred examples of other types of compound that undergo colour change reactions on irradiation are those that fall in the charge transfer category. These are compound that are colourless or of low colour when neutral but develop colour when they acquire a charge. Typically these compounds are nitrogen-comprising bases that, when protonated, form coloured compounds. Preferred examples are amines and carbazoles. These compounds are often use in combination with an acid-generating species which can be thermally or photolytically initiated or both. Suitable examples include those disclosed in WO2006/051309.

Further preferred examples of other types of compound that undergo colour change reactions on irradiation are 'leuco dyes'. Suitable leuco dyes are described in "Dyestuffs and Chemicals for Carbonless Copy Paper" presented at Coating Conference (1983, San Francisco, Calif. pp 157-165) by Dyestuffs and Chemicals Division of Ciba-Geigy Corp Greenboro, N.C. Leuco dyes are understood to be colourless in neutral or alkaline media, but become coloured when they react with an acidic or electron accepting substance. Suitable examples include compounds such as triphenylmethanephthalide compounds, azaphthalide compounds, isoindolide phthalide compounds, vinylphthalide compounds, spiropyran compounds, rhodamine lactam compounds, lactone and dilactone compounds, benzoyl leuco methylene blue (BLMB), derivatives of bis-(p-di-alkylaminoaryl)methane, xanthenes, indolyls, auramines, chromenoindol compounds, pyrollo-pyrrole compounds, fluorene compounds, and fluoran and bisfluoran compounds, with fluoran compounds being preferred. Particularly preferred commercial leuco dye products include the Pergascript range by Ciba Speciality Chemicals, Basel, Switzerland and those by Yamada Chemical Co. Ltd, Kyoto, Japan. Others include those made by Nisso Chemical Co GmbH a subsidiary of Nippon Soda Co. Ltd. Tokyo, Japan. These compounds are often use in combination with an acid-generating species which can be either thermally or photolytically initiated or both. Particularly preferred acid generating species are those that are heat stable and act via a photolytic mechanism. A preferred example of an acid-generating agent is triarylsulphonium hexafluorophosphate salts mixed in propylene carbonate.

The diacetylene compounds of the present invention can be included in a surface coating formulation such as an ink or paint. The surface coating formulation can comprise any other additives known to those skilled in the art such as binders, pigments, dyes, resins, lubricants, solubilizers, particulate matter, fluorescers, and the like. Particularly preferred are opacifying agents such as titanium dioxide, pearlescent pigments and fluorescent agents. Radiation absorbers can also be used. The surface coating formulation comprising diacetylene compounds and/or other substances of the present in invention can be applied to any substrate using any printing technique known to those skilled in the art. Examples include flexography, intaglio, gravure, screen and the like. When applied this way the diacetylenes of the present invention are comprised within a thin film on the surface of the substrate. The substrate can be any substrate known to those skilled in the art that surface coating formulations can be applied to. Examples include paper and board, plastic films, bulk plastics, metal, glass, ceramics, foodstuffs, pharmaceutical preparations and the like. Exposure of the printed substrate comprising the diacetylene compounds of the present invention to irradiation will bring about a colour change reaction which can be used to create text, artwork, devices or other images and effects.

The diacetylene compounds and/or other substances of the present invention can also be included within the bulk of the substrate. The substrate can be a solid such as a plastic or glass, a liquid, a gel, a sol, an emulsion or any other suitable phase of matter known to those skilled in the art.

Particularly preferred substrates for this type of application include thermoplastics. Examples of the thermoplastics in which the diacetylene of the present invention can be incorporated into are: arylonitrile-butadiene-styrene (ABS), acrylics, celluloids, cellulose acetate, ethylene-vinyl Acetate (EVA), ethylene-vinyl alcohol (EVAL), fluoroplastics (PTFEs, including FEP, PFA, CTFE, ECTFE, ETFE), ionomers, Kydex (a acrylic/PVC alloy), liquid crystal polymers (LCP), polyacetals (POM or acetal), polyacrylates (acrylic), polyacrylonitrile (PAN or acrylonitrile), polyamides (PA or Nylon), polyamide-imides (PAI), polyaryl ether ketones (PAEK or Ketone), polybutadienes (PBD), polybutylenes (PB), polybutylene terephthalate (PBT), polyethylene terephthalate (PET), polycyclohexylene dimethylene terephthalate (PCT), polycarbonate (PC), polyhydroxyalkanoates (PHAs), polyketones (PK), polyesters, polyethylene (PE) including low density (LDPE) and high density (HDPE) versions, polyether ether ketones (PEEK), polyetherimides (PEI), polyethersulfones (PES), polyethylene chlorinates (PEC), polyimides (PI), polylactic acid (PLA), polymethylpentene (PMP), polyphenylene oxide (PPO), polyphenylene sulfide (PPS), polyphthalamide (PPA), polypropylene (PP), polystyrene (PS), polysulfones (PSU), polyvinyl chloride (PVC), polyvinylidene chloride (PVDC) and Spectralon.

The diacetylene compounds and/or other substances of the present invention can be applied to the thermoplastic substrate using a solid or liquid masterbatch process. Suitable examples of these are supplied by Americhem Inc of Cuyahoga Falls, Ohio, USA, Hampton Colours of Stroud, UK, Riverdale Color of Perth Amboy, N.J., USA and ColorMatrix of Berea, Ohio, USA.

The diacetylene compounds and/or other substances of the present invention can be applied to the thermoplastic substrate using an injection moulding or extrusion processes such as EBM to yield a part comprising the diacetylene compounds of the present invention. This includes the formation of an intermediate perform which is then stretch blow moulded to give the desired part. These application techniques are useful for the production of containers and closures comprising the diacetylene compounds of the present invention. These containers and closures are particularly suitable for use with fast moving consumer goods, such as home and personal care products, as any data can be inscribed on to the container or closure very late down stream. This compounds of the present invention can also yield multi-colours without the need for multi-component mixtures and the user can choose which colour they desired merely by controlling the irradiation. Exposure of the part comprising the diacetylene compounds of the present invention to irradiation will bring about a colour change reaction which can be used to create text, artwork, devices or other images and effects.

The thermoplastic comprising the diacetylene compounds and/or other substances of the present in invention of the present invention can also comprise other additives known to those skilled in the art of thermoplastic processing. Particularly preferred are opacifying agents such as titanium dioxide, pearlescent pigments and fluorescent agents, and radiation absorbers such as UV and NIR absorbers. Other additives include reheat agents, slip additives, antioxidants, light and heat stabilizers, metal deactivators, PVC stabilizers, plasticizers, lubricants, PVC processing aids, impact modifiers, flame retardants, antistatic agents, fluorescent whitening agents, biostabilizers, antimicrobials, chemical blowing agents, organic peroxides nucleating agents, anti acetaldehyde agents, oxygen barriers, carbon dioxide barriers, process aids, stabilizers and HALS.

The diacetylene compounds and/or other substances of the present invention can also be included in polymers that comprise extruded films. This is particularly suitable for direct printing processes, particularly those that involve the use of lasers to initiate the colour change reactions.

The following Examples 1 and 2 illustrate compounds of the invention. Examples 3, 6, 7, 10, 11, 12a, 13a, 15, 16 and 17 illustrate their use in injection-moulding; Examples 4 and 5 in surface-coating; and Examples 8, 9, 12b, 13b and 14b in blow-moulding.

Example 1

Mono-Amide Diacetylene Compound 1

10,12-Pentacosadiynoic acid (ex. GFS Chemicals, 8.0 g) was dissolved in dichloromethane (150 ml) under a nitrogen atmosphere. To this solution oxalyl chloride (ex. Aldrich, 6.0 g) was added followed by the addition of 10 drop of DMF. The reaction mixture was then stirred at 20° C. for 4 hours.

Propargylamine (ex. GFS Chemicals, 1.27 g) dissolved in 10% aqueous sodium hydroxide solution (50 g) was added to the 10,12-pentacosadiynoic acid chloride reaction mixture over 10 minutes. The reaction mixture was then left stirring for 30 minutes at 20° C. The reaction mixture was then left to phase separate overnight. The lower DCM phase was then removed and placed in a freezer overnight. The result precipitate was collected using vacuum filtration and dried in an oven at 40° C.

The product has the formula

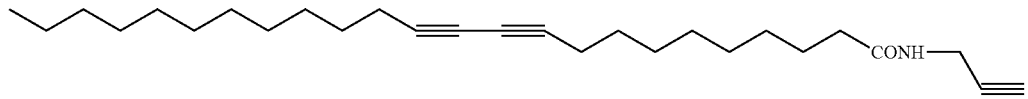

Example 2

Bis-Amide Diacetylene Compound 2

10,12-Pentacosadiynoic acid (ex. GFS Chemicals, 8.0 g) was dissolved in dichloromethane (150 ml) under a nitrogen atmosphere. To this solution oxalyl chloride (ex. Aldrich, 6.0 g) was added followed by the addition of 10 drop of DMF. The reaction mixture was then stirred at 20° C. for 4 hours.

1,8-Diaminooctane (ex. GFS Chemicals, 1.58 g) dissolved in 10% aqueous sodium hydroxide solution (50 g) was added to the 10,12-pentacosadiynoic acid chloride reaction mixture over 10 minutes. The reaction mixture was then left stirring for 30 minutes at 20° C. The resultant precipitate was collected by vacuum filtration and dried in an oven at 40° C.

The product has the formula

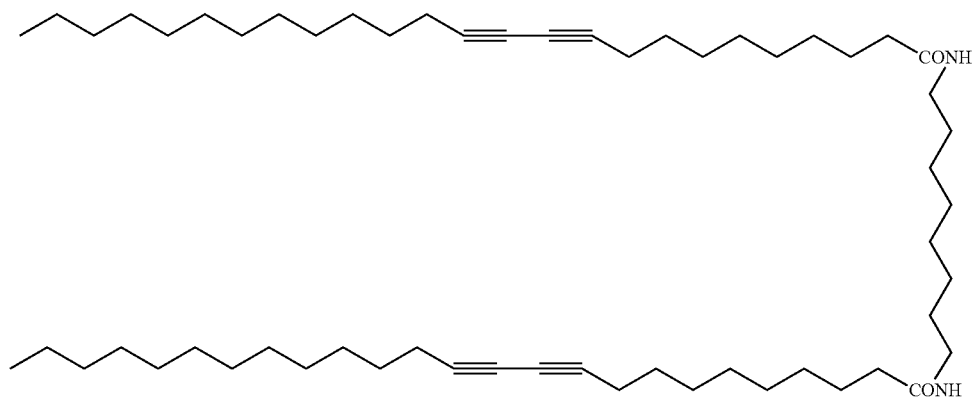

Example 3

Compounds 1 and 2 were each injection-moulded into polypropylene plaques. They had excellent coloration properties, giving deep/bright reds, magentas and blues. When Compounds 1 and 2 were replaced by analogous compounds prepared using propylamine instead of propargylamine, the PP plaques had poor coloration properties, giving weak, dirty colours.

Example 4

An ink was formulated comprising Compound 1 (5 g) and a 15% solution of Elvacite 2028 (ex. Lucite International, a low molecular weight methacrylate copolymer) in MEK (95 g). The ink formulation was milled for 10 minutes using a 50 ml Eiger-Torrance bead mill.

The ink was drawn down on to photocopy paper and HiFi 50 μm white PET film to give a coatweight of approximately 3 to 6 gsm.

Both coated substrates were initially white and turned blue on exposure to broadband ultraviolet radiation supplied by a Jenten UV curing machine. Further exposure of the coated substrate to infrared radiation using a Bosch heat gun resulted in the blue changing to a magenta, then red, then orange and then a yellow colour.

A 266 nm, 3 W UV laser linked to an IBM compatible PC was used to write text and draw artwork and devices on the coated substrate. These images could be produced in one colour or multi-coloured, depending upon the fluence applied.

Example 5

An ink was formulated comprising Compound 2 (5 g) and a 15% solution of Elvacite 2028 (ex. Lucite International, a low molecular weight methacrylate copolymer) in MEK (95 g). The ink formulation was milled for 10 minutes using a 50 ml Eiger-Torrance bead mill.

The ink was drawn down on to photocopy paper and HiFi 50 μm white PET film to give a coatweight on approximately 3 to 6 gsm.

Both coated substrates were initially white and turned blue on exposure to broadband ultraviolet radiation supplied by a Jenten UV curing machine. Further exposure of the coated substrate to infrared radiation using a Bosch heat gun resulted in the blue changing to a magenta, then red.

A 266 nm, 3 W UV laser linked to an IBM compatible PC was used to write text and draw artwork and devices on the coated substrate.

Example 6

Compound 1 (1.5 g) was mixed with Borealis HG 385 MO polypropylene (150 g). The mixture was then injection moulded using an injection moulding machine set to a barrel temperature of 220° C.

The resultant part, a closure, was initially colourless and turned blue on exposure to broadband ultraviolet radiation supplied by a Jenten UV curing machine. Further exposure of the closure to infrared radiation using a Bosch heat gun resulted in the blue changing to a magenta, then red followed by orange and yellow.

A 266 nm, 3 W UV laser linked to an IBM compatible PC was used to write text and draw artwork and devices on the closure.

Comparative Example

Example 6 was repeated, but using 10,12-pentacosadiynoic acid, instead of Compound 1.

The closure was initially colourless and a very pale blue on exposure to broadband ultraviolet radiation. Further exposure to infrared radiation using a Bosch heat gun resulted in the very pale blue changing to a very pale red.

The colours obtained were much less deep than those obtained in Example 6.

Example 7

Example 6 was repeated, but with the addition of titanium dioxide (1%).

The resultant closure was initially white and turned blue on exposure to broadband ultraviolet radiation supplied by a Jenten UV curing machine. Further exposure of the closure to infrared radiation using a Bosch heat gun resulted in the blue changing to magenta, then red followed by orange and yellow.

A 266 nm, 3 W UV laser linked to an IBM compatible PC was used to write text and draw artwork and devices on the closure.

Example 8

Compound 1 (1.5 g) was mixed with Hastalen ACP5831 D polyethylene (150 g). The mixture was then extrusion blow moulded using. An extrusion blow-moulding machine set to 190° C.

The resultant part, a bottle container, was initially colourless and turned blue on exposure to broadband ultraviolet radiation supplied by a Jenten UV curing machine. Further exposure of the closure to infrared radiation using a Bosch heat gun resulted in the blue changing to a magenta, then red followed by orange and yellow.

A 266 nm, 3 W UV laser linked to an IBM compatible PC was used to write text and draw artwork and devices on the bottle.

Example 9

Example 8 was repeated, but with the addition of titanium dioxide (1%).

The resultant bottle was initially white and turned blue on exposure to broadband ultraviolet radiation supplied by a Jenten UV curing machine. Further exposure of the closure to infrared radiation using a Bosch heat gun resulted in the blue changing to magenta, then red followed by orange and yellow.

A 266 nm, 3 W UV laser linked to an IBM compatible PC was used to write text and draw artwork and devices on the closure.

Example 10

Compound 2 (1.5 g) was mixed with Borealis HG 385 MO polypropylene (150 g). The mixture was then injection-moulded using an injection moulding machine set to a barrel temperature of 220° C.

The resultant part, a closure, was initially colourless and turned blue on exposure to broadband ultraviolet radiation supplied by a Jenten UV curing machine. Further exposure of the closure to infrared radiation using a Bosch heat gun resulted in the blue changing to magenta, then red.

A 266 nm, 3 W UV laser linked to an IBM compatible PC was used to write text and draw artwork and devices on the closure.

The colours obtained with compound 2 were much deeper than those obtained with the same amount of 10,12-PDA.

Example 11

Example 10 was repeated, but with the addition of titanium dioxide (1%).

The resultant closure was initially white and turned blue on exposure to broadband ultraviolet radiation supplied by a Jenten UV curing machine. Further exposure of the closure to infrared radiation using a Bosch heat gun resulted in the blue changing to magenta, then red.

A 266 nm, 3 W UV laser linked to an IBM compatible PC was used to write text and draw artwork and devices on the closure.

Example 12a

Compound 1 (1.5 g) was mixed with Borealis HG 385 MO polypropylene (150 g). The mixture was then injection-moulded using an injection moulding machine set to a barrel temperature of 220° C.

The resultant part, a bottle preform, was initially colourless and turned blue on exposure to broadband ultraviolet radiation supplied by a Jenten UV curing machine. Further exposure of the preform to infrared radiation using a Bosch heat gun resulted in the blue changing to magenta, then red followed by orange and yellow.

A 266 nm, 3 W UV laser linked to an IBM compatible PC was used to write text and draw artwork and devices on the preform.

Example 12b

The polypropylene preforms prepared in Example 12a were stretch-blow-moulded into bottles. This was performed with both uncoloured and coloured preforms. In each case, uncoloured areas of the results bottles were turned blue on exposure to broadband ultraviolet radiation supplied by a Jenten UV curing machine. Further exposure of the bottle to infrared radiation using a Bosch heat gun resulted in the blue changing to magenta, then red.

A 266 nm, 3 W UV laser linked to an IBM compatible PC was used to write text and draw artwork and devices on the bottle.

Example 13a

Compound 2 (1.5 g) was mixed with Borealis HG 385 MO polypropylene (150 g). The mixture was then injection moulded using an injection moulding machine set to a barrel temperature of 220° C.

The resultant part, a bottle preform, was initially colourless and turned blue on exposure to broadband ultraviolet radiation supplied by a Jenten UV curing machine. Further exposure of the preform to infrared radiation using a Bosch heat gun resulted in the blue changing to magenta, then red followed by orange and yellow.

A 266 nm, 3 W UV laser linked to an IBM compatible PC was used to write text and draw artwork and devices on the preform.

Example 13b

The polypropylene preforms prepared in Example 13a were stretch-blow-moulded into bottles. This was performed with both uncoloured and coloured preforms. In each case, uncoloured areas of the results bottles were turned blue on exposure to broadband ultraviolet radiation supplied by a Jenten UV curing machine. Further exposure of the bottle to infrared radiation using a Bosch heat gun resulted in the blue changing to magenta, then red.

A 266 nm, 3 W UV laser linked to an IBM compatible PC was used to write text and draw artwork and devices on the bottle.

Example 14a

Compound 2 (1.5 g) was mixed with Melinar B60 polyester (150 g). The mixture was then injection-moulded using an injection-moulding machine set to a barrel temperature of 280° C.

The resultant part, a bottle preform, was initially colourless and turned blue on exposure to broadband ultraviolet radiation supplied by a Jenten UV curing machine. Further exposure of the preform to infrared radiation using a Bosch heat gun resulted in the blue changing to a magenta, then red followed by orange and yellow.

A 266 nm, 3 W UV laser linked to an IBM compatible PC was used to write text and draw artwork and devices on the preform.

Example 14b

The polyester preforms prepared in Example 14a were stretch-blow-moulded into bottles. This was performed with both uncoloured and coloured preforms. In each case, uncoloured areas of the results bottles were turned blue on exposure to broadband ultraviolet radiation supplied by a Jenten UV curing machine. Further exposure of the bottle to infrared radiation using a Bosch heat gun resulted in the blue changing to magenta, then red.

A 266 nm, 3 W UV laser linked to an IBM compatible PC was used to write text and draw artwork and devices on the bottle.

Example 15

Compound 1 (1.5 g) was mixed with Hastalen ACP5831 D polyethylene (150 g), together with N-ethylcarbazole (1.5 g), triphenylamine (0.5 g) and triarylsulphonium hexafluorophosphate salts (50%) mixed in propylene carbonate (2.0 g). The mixture was then injection-moulded using an injection-moulding machine set to a barrel temperature of 190° C.

The resultant part, a closure, was initially colourless and turned blue on exposure to broadband ultraviolet radiation supplied by a Jenten UV curing machine. Further exposure of the closure to infrared radiation using a Bosch heat gun resulted in the blue changing to magenta, then red followed by orange and yellow.

On prolonged exposure to broadband UV radiation, the colourless areas turned initially blue and then green. Heating the colourless closure with a heat gun and then exposing the hot closure to broadband UV radiation resulted in the formation of a green colour.

A 266 nm, 3 W UV laser linked to an IBM compatible PC was used to write text and draw artwork and devices on the closure.

Example 16

Compound 1 (1.5 g) was mixed with Hastalen ACP5831 D polyethylene (150 g), together with Yamada Yellow Y726 (0.75 g) and triarylsulphonium hexafluorophosphate salts (50%) mixed in propylene carbonate (1.5 g). The mixture was then injection moulded using an injection-moulding machine set to a barrel temperature of 190° 0° C.

The resultant part, a closure, was initially colourless and turned blue on exposure to broadband ultraviolet radiation supplied by a Jenten UV curing machine. Further exposure of the closure to infrared radiation using a Bosch heat gun resulted in the blue changing to magenta, then red followed by orange and yellow.

On prolonged exposure to broadband UV radiation, the colourless areas turned initially blue and then green. Heating the colourless closure with a heat gun and then exposing the hot closure to broadband UV radiation resulted in the formation of a yellow colour.

A 266 nm, 3 W UV laser linked to an IBM compatible PC was used to write text and draw artwork and devices on the closure.

Example 17

Compound 2 (1.5 g) was mixed with Hastalen ACP5831 D polyethylene (150 g), together with Yamada Yellow Y726 (0.5 g) and Pergacript Blue SRB (0.5 g) and triarylsulphonium hexafluorophosphate salts (50%) mixed in propylene carbonate (2.0 g). The mixture was then injection-moulded using an injection-moulding machine set to a barrel temperature of 190° C.

The resultant part, a closure, was initially colourless and turned blue on exposure to broadband ultraviolet radiation supplied by a Jenten UV curing machine. Further exposure of the closure to infrared radiation using a Bosch heat gun resulted in the blue changing to magenta, then red followed by orange and yellow.

On prolonged exposure to broadband UV radiation, the colourless areas turned initially blue and then green. Heating the colourless closure with a heat gun and then exposing the hot closure to broadband UV radiation resulted in the formation of a green colour.

A 266 nm, 3 W UV laser linked to an IBM compatible PC was used to write text and draw artwork and devices on the closure.

The invention claimed is:

1. A compound which undergoes a colour change upon irradiation, and which has the general structure:

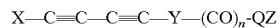

wherein X is H, alkyl or —Y—(CO)$_n$-QW; each Y is the same or a different divalent alkylene group; Q is O, S or NR; R is H or alkyl; W is H, alkyl or Z; each Z is the same or a different unsaturated alkyl group and includes —C≡CH; and each n is 0 or 1.

2. The compound according to claim 1, wherein Z is propargyl, alkylpropargyl or dialkylpropargyl.

3. The compound according to claim 2, wherein Q and Z are such that H-Q-Z is propargyl alcohol; propargylamine; dipropargylamine; tripropargylamine; 1,1-dimethylpropargylamine; propargyl thiol; or 1,1-dimethylpropargyl alcohol.

4. The compound according to claim 1, wherein X is $(CH_2)_{11}CH_3$ and Y is $(CH_2)_8$.

5. The compound according to claim 1, wherein Q is NR.

6. The compound according to claim 1, wherein X is H or alkyl.

7. A composition comprising a compound according to claim 1, and at least one other substance capable of changing colour upon irradiation.

8. The composition according to claim 7, wherein the other substance is a charge transfer agent.

9. The composition according to claim 8, wherein the charge transfer agent is a compound that comprises at least one nitrogen atom.

10. The composition according to claim 9, wherein the charge transfer agent is an aromatic amine.

11. The composition according to claim 10, wherein the charge transfer agent is a carbazole.

12. The composition according to claim 7, wherein the other substance is a leuco dye.

13. The composition according to claim 7, which additionally comprises a photoacid-generating agent.

14. The composition according to claim 7, which additionally comprises one or more additives selected from an opacifying agent, a pearlescent or fluorescent agent and a radiation-absorbing substance.

15. A method of imparting colour to a material including a compound according to claim 1, which comprises subjecting the material to irradiation.

16. The method according to claim 15, wherein the irradiation is ultraviolet irradiation.

17. The method according to claim 15, wherein irradiation is ultraviolet irradiation followed by infrared irradiation.

18. The method according to claim 15, wherein the irradiation is laser or non-coherent radiation.

* * * * *